US006411064B1

(12) United States Patent
Brink

(10) Patent No.: US 6,411,064 B1
(45) Date of Patent: Jun. 25, 2002

(54) SYSTEM AND METHOD FOR CHARGING A CAPACITOR USING A VARIABLE FREQUENCY, VARIABLE DUTY CYCLE CURRENT WAVEFORM

(75) Inventor: Gregory D. Brink, Port Townsend, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 41 days.

(21) Appl. No.: 09/619,954

(22) Filed: Jul. 20, 2000

(51) Int. Cl.[7] ................................................. H02L 7/00

(52) U.S. Cl. ....................................................... 320/166

(58) Field of Search ................................... 320/166, 167

(56) References Cited

U.S. PATENT DOCUMENTS 4,598,198 A * 7/1986 Fayfield ....................... 250/205

OTHER PUBLICATIONS

IBM Technical Disclosure Bulletin, Variable Frequency–Duty Cycle Slow Start Control for Switched–Mode Power Supplies, Mar. 1, 1989, vol. 31, issue 10, pp. 252–254.*

* cited by examiner

Primary Examiner—Gregory Toatley

(57) ABSTRACT

A system and method for charging a high-voltage capacitor through the application of a current, the magnitude of which has a variable frequency, variable duty cycle waveform. Generally, energy is transferred from a power source to the high voltage capacitor via a magnetic element such as an inductor or transformer. For example, a pulsed voltage supply provides voltage pulses having a variable frequency and an adjustable duty cycle to a primary winding of a fly-back transformer. During a charging sequence in which current charge cycles are applied to the capacitor, the duty cycle of the variable frequency current waveform is controlled dynamically based on the rate at which energy can be transferred to the capacitor. Specifically, during a charge sequence, current pulses through the primary winding are controlled such that the transformer operates in a continuous mode during an initial portion of the charge sequence, and in a discontinuous mode during a subsequent portion of the charge sequence. During the continuous mode, the duration of the off or non-conduction time of the primary winding current waveform is limited to be less than or equal to a maximum time period. Within this maximum time period energy can be transferred efficiently from the transformer to the capacitor. Subsequent, inefficient conduction time is inhibited. This increases the speed at which the high voltage capacitor is charged.

13 Claims, 7 Drawing Sheets

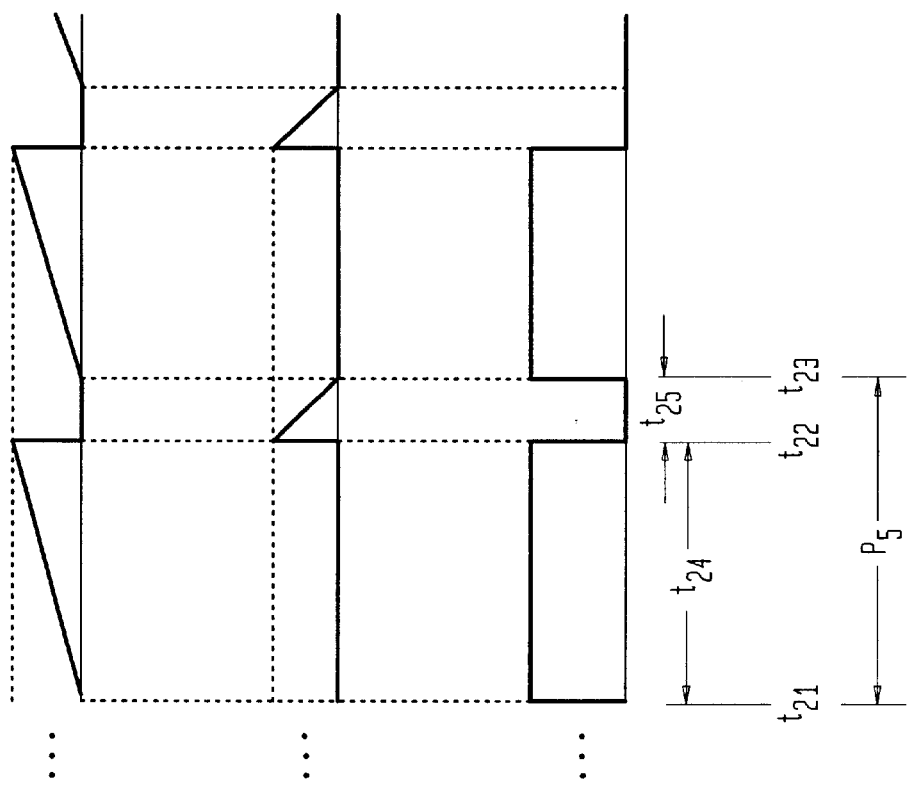
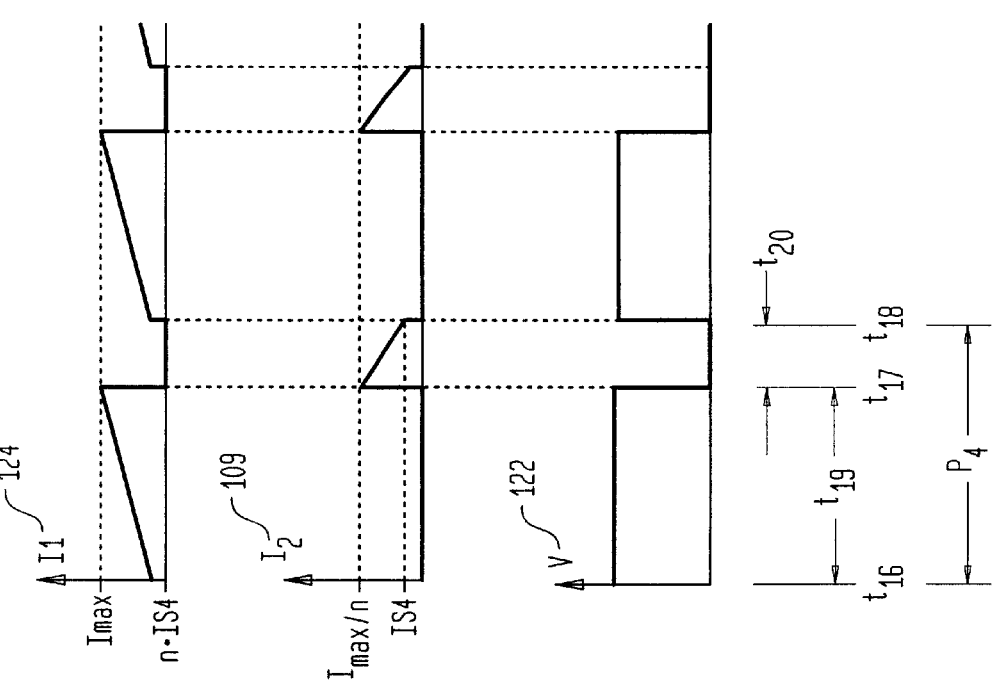

SYSTEM AND METHOD FOR CHARGING A CAPACITOR USING A VARIABLE FREQUENCY, VARIABLE DUTY CYCLE CURRENT WAVEFORM

RELATED APPLICATIONS

The following application is related to the present application and its disclosure is incorporated herein by reference:

U.S. Utility patent application Ser. No. 09/620,446 entitled "System and Method for Charging A Capacitor Using a Constant Frequency Current Waveform," and naming as inventor Gregory D. Brink.

BACKGROUND OF THE INVENTION

1. Field of the Invention

The present invention relates generally to charging capacitors and, more particularly, to a method and apparatus for charging high voltage capacitors.

2. Related Art

Sudden cardiac arrest has been attributed to over 350,000 deaths each year in the United States, making it one of the country's leading medical emergencies. Worldwide, sudden cardiac arrest has been attributed to a much larger number of deaths each year. One of the most common and life threatening consequences of a heart attack is the development of a cardiac arrhythmia, commonly referred to as ventricular fibrillation. When in ventricular fibrillation, the heart muscle is unable to pump a sufficient volume of blood to the body and brain. The lack of blood and oxygen to the brain may result in brain damage, paralysis or death to the victim.

The probability of surviving a heart attack or other serious heart arrhythmia depends on the speed with which effective medical treatment is provided. If prompt cardiopulmonary resuscitation is followed by defibrillation within approximately four minutes of the onset of symptoms, the probability of survival can approach or exceed fifty percent. Prompt administration of defibrillation within the first critical minutes is, therefore, considered one of the most important components of emergency medical treatment for preventing death from sudden cardiac arrest.

Cardiac defibrillation is an electric shock that is used to arrest the chaotic cardiac contractions that occur during ventricular fibrillation, and to restore a normal cardiac rhythm. To administer such an electrical shock to the heart, defibrillator pads are placed on the victim's chest, and an electrical impulse of the proper magnitude and shape is administered to the victim through the pads. While defibrillators have been known for years, they have typically been complicated, making them suitable for use by trained personnel only.

More recently, portable and transportable automatic and semi-automatic external defibrillators (generally, AEDs) for use by first responders have been developed. A portable defibrillator allows proper medical care to be given to a victim earlier than preceding defibrillators, increasing the likelihood of survival. Such portable defibrillators may be brought to or stored in an accessible location at a business, home, aircraft or the like, available for use by first responders. With recent advances in technology, even a minimally trained individual can operate conventional portable defibrillators to aid a victim in the critical first few minutes subsequent to the onset of sudden cardiac arrest.

As noted, effective medical treatment must be administered promptly after the onset of symptoms. One time consuming defibrillator operation is the charging of a high voltage capacitor that provides the energy for producing the electric shock. Unfortunately, conventional AEDs do not efficiently charge the high voltage capacitor, consuming valuable time preparing to provide the therapy. This limits the number of multiple shocks that can be administered to a patient in the minimal time available. What is needed, therefore, is a defibrillator that can charge a high voltage capacitor quickly and efficiently.

SUMMARY OF THE INVENTION

The present invention is a system and method for charging a high-voltage capacitor through the application of a current, the magnitude of which has a variable frequency, variable duty cycle waveform. Generally, energy is transferred from a power source to the high voltage capacitor via a magnetic element such as an inductor or transformer. For example, a pulsed voltage supply provides voltage pulses having a variable frequency and an adjustable duty cycle to a primary winding of a fly-back transformer.

During a charging sequence in which current charge cycles are applied to the capacitor, the duty cycle of the variable frequency current waveform is controlled dynamically based on the rate at which energy can be transferred to the capacitor. Specifically, during a charge sequence, current pulses through the primary winding are controlled such that the transformer operates in a continuous mode during an initial portion of the charge sequence, and, to the extent necessary to fully charge the capacitor, in a discontinuous mode during a subsequent portion of the charge sequence. During the continuous mode, the duration of the off or non-conduction time of the primary winding current waveform is limited to be less than or equal to a maximum time period. Within this maximum time period energy can be transferred efficiently from the transformer to the capacitor. Subsequent, inefficient conduction time is inhibited. This increases the speed at which the high voltage capacitor is charged.

A number of aspects of the invention are summarized below, along with different embodiments that may be implemented for each of the summarized aspects. It should be understood that the summarized embodiments are not necessarily inclusive or exclusive of each other and may be combined in any manner in connection with the same or different aspects that is non-conflicting and otherwise possible. These disclosed aspects of the invention, which are directed primarily to high performance capacitor charging systems and methodologies, are exemplary aspects only and are also to be considered non-limiting.

In one aspect of the invention, a capacitor charging system connected electrically to a high voltage capacitor is disclosed. The capacitor charging system is constructed and arranged to charge the capacitor by generating a variable frequency, variable duty cycle current waveform. In one embodiment, the system generates a charge sequence of successive current charge cycles, and includes a transformer and a controller. The transformer has a primary winding connected in series to a voltage source and a secondary winding across which the capacitor is electrically coupled. The controller controls a primary current through the primary winding such that during each of a first plurality of charge cycles the transformer does not transfer all stored energy to the capacitor, and during each of a subsequent plurality of charge cycles the transformer transfers substantially all stored energy to the capacitor. In one implementation, the transformer may be a fly-back transformer. In such an implementation the controller can include two current detectors. A first current detector determines when the primary current achieves a maximum current while the second current detector determines when current flowing through the secondary winding falls below a minimum current. The controller controls the primary current based at least in part on these conditions of the primary and secondary winding current.

In another aspect of the invention a system for charging a high-voltage capacitor is disclosed. The system includes a fly-back transformer having a primary winding, a core and a secondary winding that is out of phase with the primary winding. The capacitor is electrically coupled across the secondary winding. A charge controller is also included. The charge controller applies a charge sequence of successive current charge cycles to the primary winding. Each charge cycle has an on time and an off time. For each charge cycle on time the controller enables the primary current to flow through the primary winding until the primary current reaches a maximum current. For each charge cycle off time the controller inhibits the primary current until either current through the secondary winding is approximately zero or a maximum charge cycle off time has transpired. In operation, for a first plurality of charge cycles the maximum off time transpires prior to the secondary winding current becoming approximately zero, resulting in the transformer storing energy during each of the first plurality of charge cycles. For a second plurality of charge cycles occurring subsequent to the first plurality of charge cycles, the secondary winding current becomes zero prior to the maximum off time transpiring, resulting in the transformer transferring substantially all stored energy to the capacitor during the second plurality of charge cycles.

In a further aspect, a high-voltage capacitor charging system is disclosed. The system generates current pulses having a variable frequency to charge a capacitor. During a charging sequence in which the current pulses are repeatedly applied to the capacitor, the duty cycle of the variable frequency current waveform is controlled dynamically based on the rate at which energy can be transferred to the high voltage capacitor.

In a still further aspect of the invention a method for charging a capacitor is disclosed. The method includes the steps of providing a fly-back transformer having a primary winding, a core and a secondary winding that is out of phase with the primary winding; and applying a charge sequence of successive current charge cycles to the primary winding. The latter step is performed such that for each charge cycle on time the primary current is applied until the primary current reaches a maximum current, and for each charge cycle off time the primary current is inhibited until either current through the secondary winding is approximately zero or a maximum charge cycle off time has transpired.

In one embodiment, the maximum charge cycle off time is of a duration such that for a first plurality of charge cycles the maximum off time transpires prior to the secondary winding current becomes approximately zero, resulting in the transformer storing energy during each of the first plurality of charge cycles, and for a second plurality of charge cycles occurring subsequent to the first plurality of charge cycles, the secondary winding current becomes zero prior to the maximum off time transpiring, resulting in the transformer transferring substantially all stored energy to the capacitor during the second plurality of charge cycles.

Various embodiments of the present invention provide certain advantages and overcome certain drawbacks of the conventional techniques. Not all embodiments of the invention share the same advantages and those that do may not share them under all circumstances. This being said, the present invention provides numerous advantages including the noted advantage of efficiently transferring energy to a high voltage capacitor. Alternative or additional significant benefits may be realized depending on the desired application. For example, systems implementing the present invention can provide charge times comparable to conventional systems using smaller components, a lower energy power source, a higher impedance power source or any reasonable combination thereof. These and other features and advantages of the present invention as well as the structure and operation of various embodiments of the present invention are described in detail below with reference to the accompanying drawings.

BRIEF DESCRIPTION OF THE DRAWINGS

This invention is pointed out with particularity in the appended claims. The above and further features and advantages of this invention may be better understood by referring to the following description when taken in conjunction with the accompanying drawings. In the drawings, like reference numerals indicate identical or functionally similar elements. Additionally, the left most one or two digits of a reference numeral identify the figure in which the reference numeral first appears. In the drawings:

FIGS. 2A–2G are exemplary waveforms generated in accordance with in one embodiment of the present invention.

DETAILED DESCRIPTION

Figure 1:
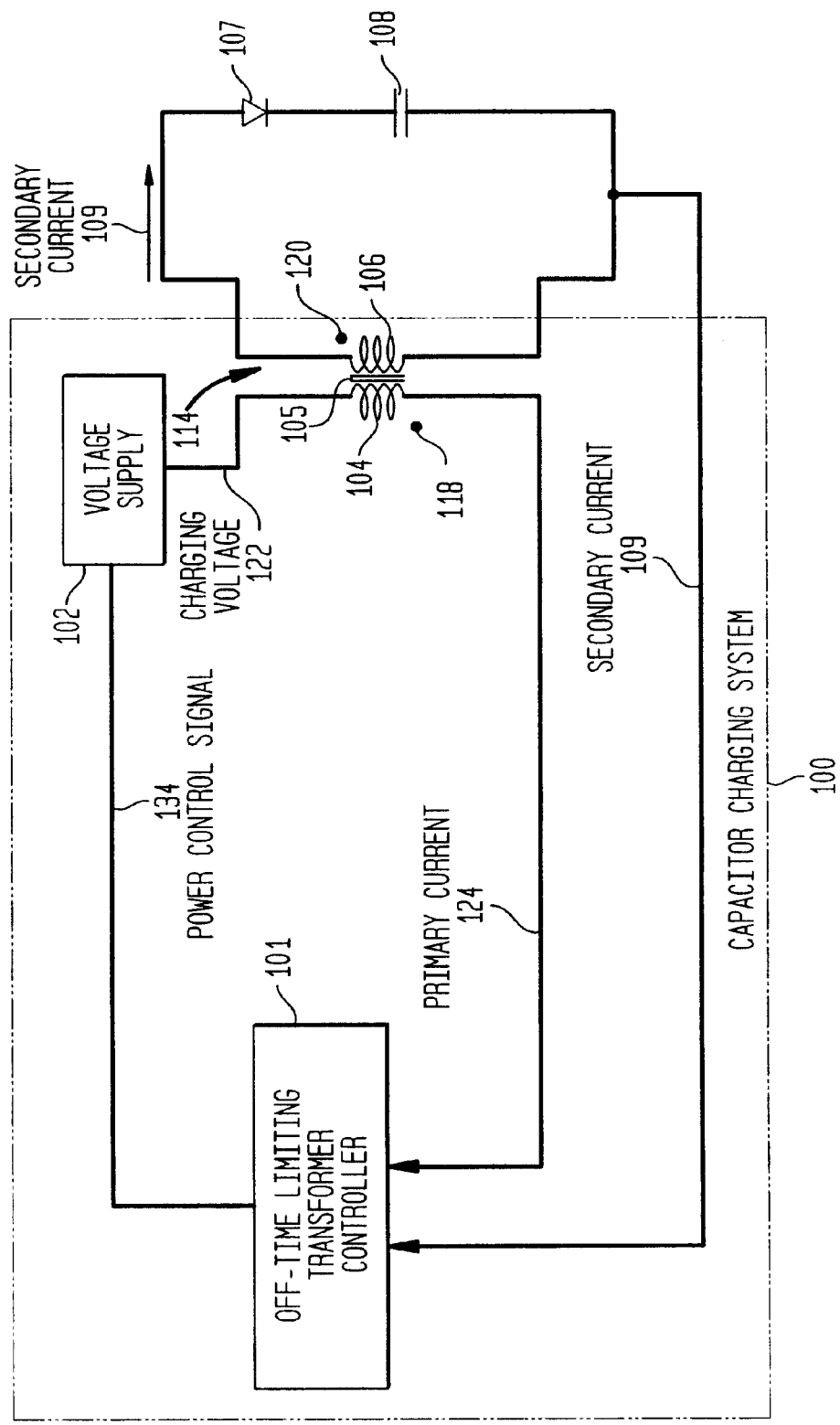
FIG. 1A is a high-level block diagram of a capacitor charging system in accordance with one embodiment of the present invention.
FIG. 1B is a block diagram of one embodiment of the capacitor charging circuit of the present invention.

FIG. 1A is a high-level block diagram of a capacitor charging system in accordance with one embodiment of the present invention. Capacitor charging system 100 generates a current 109 the magnitude of which has a variable frequency, variable duty cycle waveform. During a charging sequence in which multiple charge cycles of current 109 are applied to high voltage capacitor 108, the duty cycle and frequency of the charge cycles are controlled to prevent the inefficient transfer of energy caused by, for example, low capacitor voltages, thereby accelerating the speed at which capacitor 108 is charged.

As will be described in greater detail below, the present invention may utilize a magnetic element to transfer energy to a high voltage capacitor. FIG. 1B is a block diagram of one embodiment of a capacitor charging system 100 of the present invention utilizing a magnetic element. In this illustrative embodiment, capacitor charging system 100 includes a transformer 114 as such a magnetic element. Capacitor charging transformer 114 includes a core 105, primary winding 104 and secondary winding 106. In the particular embodiment illustrated in FIG. 1B, primary winding 104 and secondary winding 106 form a fly-back transformer and, therefore, are out of phase with each other. This is shown by the polarity indicating indicia 118 and 120. As such, the following description sets forth various embodiments and components of system 100 for driving a fly-back transformer to generate current waveform 109. Such a current 109 flows through secondary winding 106 in the direction shown to transfer energy to capacitor 108 which is connected across secondary winding 106 through a high voltage rectifier diode, referred to herein as fly-back diode 107. It should become apparent from the present disclosure that other magnetic elements as well as other current generators may be utilized in accordance with the teachings of the present invention.

Primary winding 104 transfers energy from a power source to transformer core 105 when current flows through primary winding 104. Similarly, secondary winding 106 transfers energy from transformer core 105 to capacitor 108 when secondary current 109 is flowing through secondary winding 106. As primary current 124 flows through primary winding 104, secondary current 109 does not flow through secondary winding 106 due to the opposing polarity of the windings. Energy that is transferred from power source 102 to transformer core 105, then, is not transferred immediately to capacitor 108; instead the energy is stored within transformer core 105. As a result, the energy stored in transformer core 105 accumulates as primary current 124 flows through primary winding 104. Conversely, when primary current 124 does not flow through primary winding 104, secondary current 109 flows through secondary winding 106. When this occurs, energy previously stored in transformer core 105 is transferred to capacitor 108, thereby charging capacitor 108.

In accordance with embodiments of the present invention, the conduction time of each cycle of secondary current 109 is limited to a maximum duration to efficiently transfer energy to capacitor 108. The elimination of inefficient energy transfer by limiting the charge cycle off time to a maximum time duration is described in detail below. The rate at which energy is delivered to capacitor 108 is proportional to the voltage currently stored in the capacitor. Because the voltage in a high voltage capacitor may be increased from zero to several thousand volts, the energy transfer rate will vary throughout a charge sequence. Early in a capacitor charge sequence there is a minimum capacitor voltage. This results in a low energy transfer rate and, therefore, a very long discharge cycle during which energy is transferred from secondary winding 106 to capacitor 108. As a result, the conduction time is characterized by varying degrees of energy transfer efficiency. Initially, significant energy is transferred to capacitor 108. As the conduction time continues, the energy transfer rate decreases thereby decreasing the transfer efficiency. To avoid this inefficiency which occurs latter in the conduction time portion of a charge cycle, the duration of the each charge cycle conduction time is limited to a predetermined maximum time duration that permits the efficient energy transfer to occur while inhibiting the latter, efficient energy transfer from occurring.

This maximum time duration is selected based on a tradeoff between the rate of energy transfer and the need to accumulate energy in capacitor 108. In one embodiment, this maximum time duration is substantially less than the time necessary to completely transfer all energy from transformer core 105 to capacitor 108 in a single charge cycle when capacitor 108 has minimal stored energy. In such an embodiment, the present invention curtails the discharge cycle, preventing the complete transfer of stored energy from transformer core 105. The energy that is not transferred to capacitor 108 remains stored in transformer core 105. Accordingly, this portion of the charge sequence is referred to as the continuous mode due to the continuous storage of energy in transformer core 105. As the charging process continues and the capacitor charge increases, the rate at which energy is transferred from secondary winding 106 to capacitor 108 increases as well. This, in turn, increases the amount of energy transferred to capacitor 108 within the predetermined maximum conduction time. If capacitor 108 is not fully charged, then at some time during a charge sequence, all energy can be transferred from transformer core 105 to capacitor 108 during a single charge cycle. This marks the beginning of the discontinuous mode of operation, which continues until capacitor 108 is fully charged.

From the perspective of capacitor charging system 100, direct control of primary winding 104 is provided to achieve the above operations; that is, the above operations are accomplished by controlling the duty cycle and frequency of primary current 122. From this perspective, it is the off-time of primary current 124 that is limited to the noted predetermined maximum time duration. Accordingly, the following description refers to the conduction of primary current 124 through primary winding 104. Each charge cycle of primary current 124 is referred to as having an "on" or "conduction" time during which current is flowing through primary winding 104, and an "off" or "non-conduction" time during which current is not flowing through primary winding 104. Stated another way, the disclosed embodiment of the present invention limits the off time of individual charge cycles of primary current 124 to a predetermined maximum time duration. In the disclosed embodiment, charging system 100 includes a voltage supply 102 series connected to primary winding 104 of capacitor charging transformer 114 and controlled by transformer controller 101. In this embodiment, secondary current waveform 109 is generated by controlling the voltage applied to primary winding 104. Thus, voltage supply 102 generates a charging voltage 122 also having a variable frequency, variable duty cycle waveform.

As noted, the inefficient off time of the primary current charge cycle is limited to some predetermined maximum time duration to substantially limit or eliminate the time consuming and inefficient portion of each such charge cycle. Limiting the conduction time and initially driving transformer 114 in a continuous mode eliminates the potion of each charge cycle during which minimal energy transfer is achieved over a significant time period due to the minimal charge stored in capacitor 108. Additional conduction time-limited charge cycles can then be applied, with a greater quantity of energy being transferred during each subsequent charge cycle. As the charge sequence continues and the capacitor charge increases, the rate at which energy is transferred from secondary winding 106 to capacitor 108 increases. When the capacitor charge is sufficient to enable transformer 114 to completely transfer its stored energy to capacitor 108 within the maximum time duration, a second, subsequent portion of the charge sequence begins wherein all energy is transferred from transformer 114 to capacitor 108 during each charge cycle. As noted, this latter portion of the charge sequence is referred to as the discontinuous mode of operation since energy is no longer stored continuously in transformer core 105. The charge sequence continues with the off time of each charge cycle continually decreasing until capacitor 108 is fully charged during the off-time of a single charge cycle.

FIGS. 2A–2G are exemplary waveforms generated during a charging sequence in accordance with one embodiment of the present invention. Each of the exemplary waveform figures includes, for a particular relative time period, primary current 124 flowing in primary winding 104, secondary current 109 flowing in secondary winding 106 and charging voltage 122 applied to primary winding 104. The waveforms illustrated in FIG. 2A occur prior to the waveforms illustrated in FIG. 2B which themselves occur prior to those illustrated in FIG. 2C and so on. Thus, there is a progression in time beginning with FIG. 2A and culminating with FIG. 2G. The sequential nature of these waveforms is represented by a series of dots interposed between neighboring time intervals of each waveform. To clearly illustrate the relationship between applied voltage 122, primary current 124 and secondary current 109, each Figure includes two complete cycles of each waveform for the relevant time period.

The waveforms in FIGS. 2A–2G illustrate the application of primary voltage 122 such that capacitor charger 100 generates a variable frequency charging current 109 having a variable duty cycle that substantially eliminates inefficient energy transfer conditions. Generally, FIGS. 2A–2D depict a series of waveforms that occur during the first portion of a charge sequence in which transformer 114 is operated in accordance with the continuous mode of operation. During the continuous mode, the portion of each charge cycle during which energy is transferred from transformer 114 to capacitor 108 is limited to a maximum time duration that is less than the time required to achieve a complete transfer of energy. As noted, in the disclosed embodiment, this is achieved by limiting the "off time" of the current flowing through primary winding 104 of fly-back transformer 114, causing a similar restriction to the on time of the secondary current waveform. This results in the accumulation of energy in transformer core 105 over successive charge cycles while energy is also being transferred to capacitor 108. As the energy in capacitor 108 increases, so too does the rate at which energy is transferred from transformer 114 to capacitor 108. In response to this well-known phenomenon, there is a concomitant increase in the time required to transfer energy to transformer 114 to replace the energy provided to capacitor 108. That is, the on-time of each cycle of primary current 124, which is not restricted, increases. This increases the period, and decreases the frequency, of successive charge cycles.

Figure 2A:
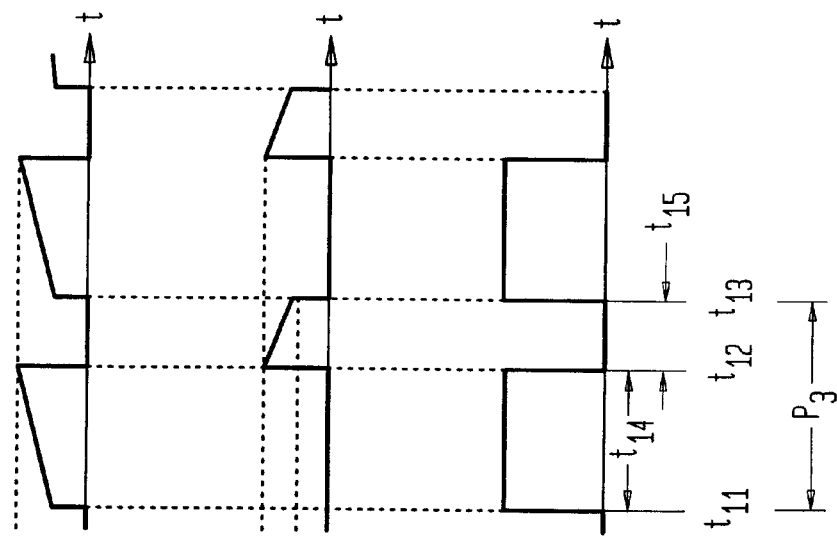

The energy transferred to capacitor 108 is initially stored in transformer core 105. Referring to FIG. 2A, the rate at which the energy is transferred into transformer core 105 is substantially constant throughout the charge cycles, as shown by the constant slope of the primary current waveforms in FIGS. 2A through 2G. On the other hand, the rate of energy transfer from transformer core 105 to capacitor 108 increases as the capacitor voltage increases. This is shown by the increasing negative slope of secondary current waveform 109 illustrated in FIGS. 2A–2G.

Initially, transformer core 105 has minimal or no energy stored therein. To store a desired quantity of energy in transformer core 105, primary current 124 is ramped from zero to a predetermined maximum value $I_{max}$ immediately upon the invocation of a charging sequence. The waveforms illustrated in FIGS. 2A–2G occur subsequent to this initial storage of energy in transformer core 105.

The duty cycle of the primary and secondary current waveforms is adjusted to maintain transformer 114 in a continuous conduction mode of operation throughout this initial portion of the charging sequence. The current that flows through each winding during a charging cycle is a function of the turns ratio, n, of transformer 114. Generally, primary current 124 starts at a value that is equivalent to the product of the turns ratio and secondary current 109 at the end of the immediately previous charge cycle. Primary current 124 ramps from this value to $I_{max}$ during the first portion of the charge cycle. Similarly, for each charge cycle, secondary current 109 is equivalent to the immediately occurring primary current 124 divided by the turns ratio. Secondary current 109 ramps down from this value to some lower value over the remaining portion of the charge cycle.

Referring to the FIGS. 2A–2D, charging voltage 122 is applied to primary winding 104 for time duration $t_4$ beginning at time $t_1$, and ceasing at time $t_2$. At time $t_2$, primary current 124 has reached the maximum value $I_{max}$. In response, application of pulsed voltage supply 102 ceases at time $t_2$ as shown by the falling edge of charging voltage waveform 122. At this time, primary winding current 124 falls to zero and secondary current 109 in secondary winding 106 rises to a level of $I_{max}/n$, where n is the turns ratio of transformer 114. Secondary current 109 begins to decrease as the energy stored in transformer core 105 is transferred to capacitor 108. This occurs for time duration $t_5$. As noted, in this embodiment, secondary winding 106 is out of phase with primary winding 104 and, therefore, transfers energy when primary winding 104 is not being charged; that is, time period $t_5$. Time period $t_4$ and time period $t_5$ occur during one charge cycle defined by one period $P_1$ of charging voltage 122.

As noted, the energy transfer rate; that is, the absolute value of the magnitude of the slope of secondary current waveform 109 during time period $t_5$ is proportional to the capacitor voltage. During this time period, secondary current 109 decreases from $I_{max}/n$ to $I_{s1}$. At time $t_3$ main charging voltage 122 is applied once again to primary winding 104. This, in turn, causes current to flow through primary winding 104, and discontinues the discharge of secondary winding 106. This is shown by primary current waveform 124 linearly increasing, not from a zero current value, but from initial condition $n*I_{s1}$, where n is the turns ratio of transformer 114.

Figure 2B:
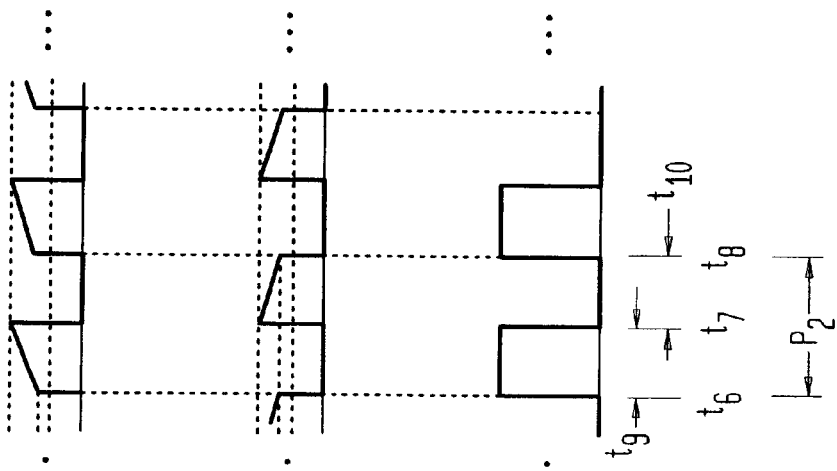

FIG. 2B shows the same waveforms at some later time at which the capacitor voltage is greater than during time intervals $t_4$ and $t_5$. Charging voltage 122 is applied to primary winding 104 for time duration $t_9$ beginning at time $t_6$ and ceasing at time $t_7$. At time $t_6$, primary current 124 linearly increases from initial condition $n*I_{s2}$ to $I_{max}$. At time $t_7$, primary current 124 has reached the predetermined maximum value $I_{max}$. In response, pulsed voltage supply 102 is turned off at time $t_7$ as shown by the falling edge of charging voltage waveform 122. At this time, primary winding current 124 falls to zero and secondary current 109 in secondary winding 106 rises to a level of $I_{max}/n$. Secondary current 109 begins to decrease as the energy stored in transformer core 105 is transferred to capacitor 108. This occurs for time duration $t_{10}$ during which secondary current 109 decreases from $I_{max}/n$ to $I_{s2}$. Comparison with the secondary waveform occurring at time interval $t_5$ of FIG. 2A illustrates a change in slope of secondary current 109. This change in slope reflects the increased energy transfer rate now possible given the increased capacitor voltage. As a result, secondary current 109 decreases from $I_{max}/n$ to $I_{s2}$ where $I_{s2}$ is less than $I_{s1}$ during a time interval $t_{10}$ that is limited to the same maximum duration as time interval $t_5$.

At time $t_8$, charging voltage 122 is again applied to primary winding 104, as shown in FIG. 2B. This, in turn, causes current to flow through primary winding 104, and discontinues the discharging of secondary winding 106. This is shown by primary current waveform 124 linearly increasing from initial condition n*$I_{s2}$, where n is the turns ratio of transformer 114. It should be noted that, in response to the increased rate at which energy is transferred to capacitor 108 during the fixed time period $t_{10}$ as compared with time interval $t_5$, the duration of time period $t_9$ is greater than that of $t_4$ to transfer the additional energy necessary to fully charge transformer core 105.

Figure 2C:
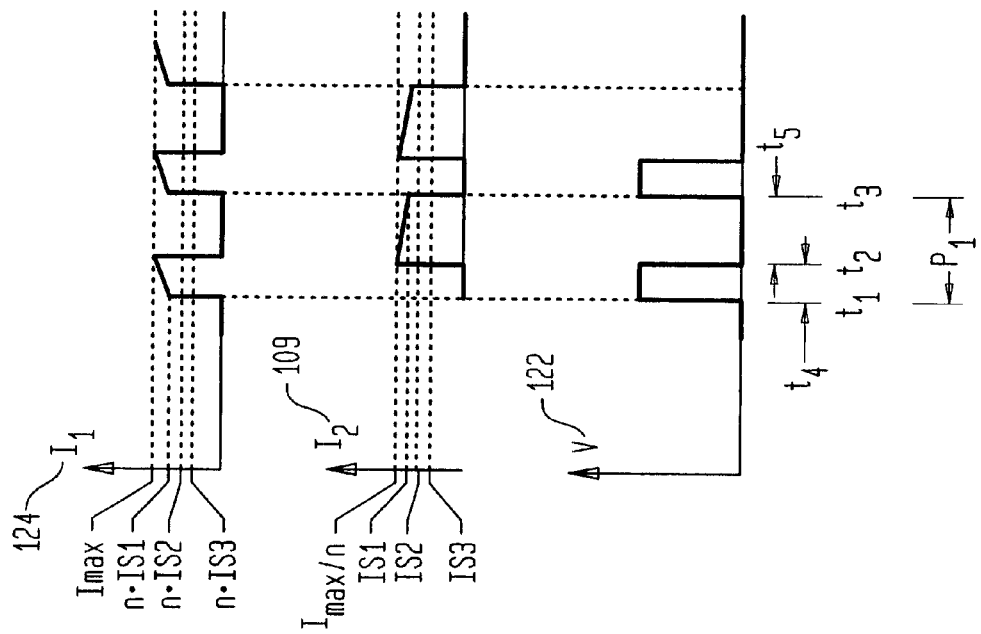

FIG. 2C shows the respective waveforms at some still later time at which the capacitor voltage is greater than during time intervals $t_4$, $t_5$ and $t_9$, $t_{10}$. At the latter time $t_{11}$, charging voltage 122 is applied to primary winding 104 for time duration $t_{14}$ beginning at time $t_{11}$ and ceasing at time $t_{12}$. At time $t_{12}$, primary current 124 has reached the maximum value $I_{max}$. In response, pulsed voltage supply 102 is turned off at time $t_{12}$ and primary winding current 124 falls to zero. Secondary current 109 rises to a level of $I_{max}/n$ at time $t_{12}$. Secondary current 109 decreases from $I_{max}/n$ to $I_{s3}$ during time duration $t_{15}$ as the energy stored in transformer core 105 is transferred to capacitor 108. Comparison with secondary waveform 109 occurring at time intervals $t_5$ and $t_{10}$ illustrates a continuing change in slope of secondary current 109 reflecting the continued increase in capacitor voltage. As a result, secondary current 109 decreases from $I_{max}$ to $I_{s3}$ which is less than $I_{s2}$ during a time interval $t_{15}$ which is less than time interval $t_{10}$. At time $t_{13}$, main charging voltage 122 increases causing current to flow through primary winding 104, and causing current to discontinue flowing through secondary winding 106. This is shown by primary current waveform 124 linearly increasing from initial condition n*$I_{s3}$.

The time to charge primary winding 104 to $I_{max}$, that is, time durations $t_4$, $t_9$, and $t_{14}$ are successively longer time periods. Conversely, the time to discharge secondary winding 106 from $I_{max}/n$ to $I_{s2}$, time durations $t_5$, $t_{10}$, and $t_{15}$ are limited to some maximum time duration. This insures transformer core 105 accumulates stored energy during the charging sequence as the energy transfer rate from transformer core 105 to capacitor 108 increases, while rapidly transferring energy from transformer core 105 to capacitor 108. This is a characteristic of a transformer operating in accordance with the present invention; that is, in the continuous mode of operation wherein only the energy removed from transformer 114 is replaced, and transformer 114 is maintained so as to continually store energy.

As noted, the duration of each charge cycle during this first portion of the charge sequence limits the off time of the primary current waveform. Referring to FIGS. 2A–2E, this is illustrated by the time periods $t_5$, $t_{10}$, $t_{15}$, $t_{20}$ and $t_{25}$ being of the same duration. It was also noted that the period of the charge cycle increases in response to the increased time utilized to replace the transferred energy during successive charge cycles. This is illustrated by the waveforms of FIGS. 2A–2E having corresponding time periods $t_4 < t_9 < t_{14} < t_{19} < t_{24}$ and the periods of the same waveforms in each of the successive figures is increasing; that is $P_1 < P_2 < P_3 < P_4 < P_5$. The continuous mode of operation then, facilitates the rapid charging of capacitor 108 through the prevention of long duration discharges from transformer 114 to capacitor 108.

This progression continues until capacitor 108 has sufficient stored energy such that the energy transfer rate is great enough to transfer all transformer energy to capacitor 108 in a single charge cycle. This condition, which is illustrated in FIG. 2E, marks the transition from continuous transfer mode to discontinuous transfer mode. Referring now to FIG. 2E, at time $t_{21}$, charging voltage 122 is applied to primary winding 104 for time duration $t_{24}$, ceasing at time $t_{22}$. At time $t_{22}$, primary current 124 has reached the predetermined maximum value $I_{max}$. In response, pulsed voltage supply 102 is turned off at time $t_{22}$ and primary winding current 124 falls to zero. Secondary current 109 rises to a level of $I_{max}/n$ at time $t_{22}$. Secondary current 109 decreases from $I_{max}/n$ to zero during time duration $t_{25}$ as substantially all of the energy stored in transformer core 105 is transferred to capacitor 108. The continuing negative slope of secondary current 109 culminates to the illustrated condition wherein the energy transfer rate is sufficiently great to transfer all energy stored in transformer core 105 to capacitor 108 during fixed time interval $t_{25}$. At time $t_{23}$, charging voltage 122 is again applied to primary winding 104 causing current to flow through primary winding 104, and current to discontinue flowing through secondary winding 106. This is shown by primary current waveform 124 linearly increasing from initial condition of zero to $I_{max}$.

Figure 2G:
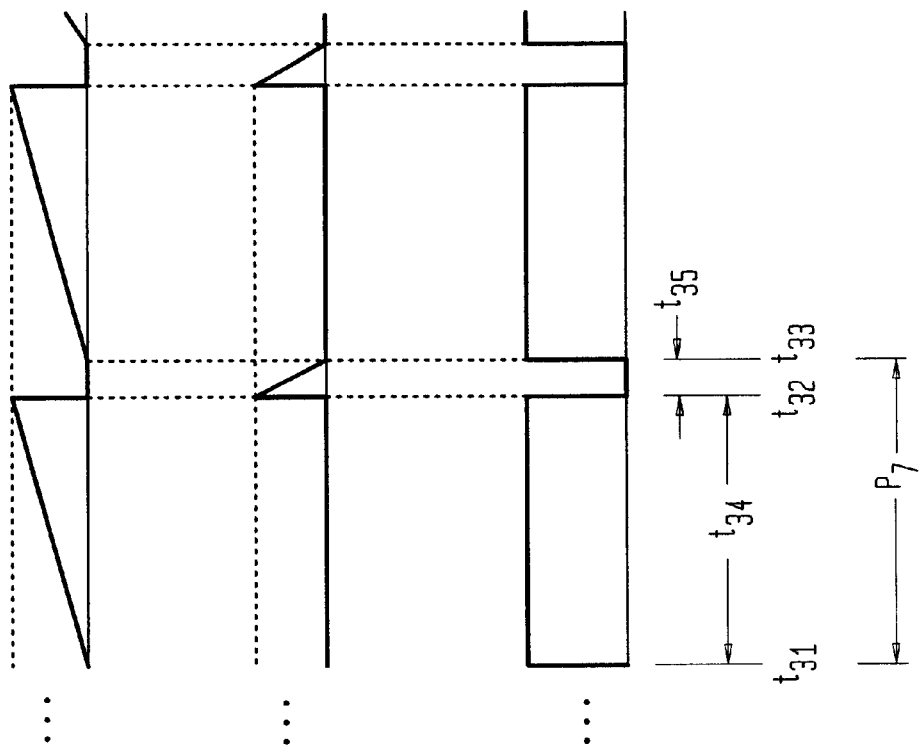
Figure 2F:
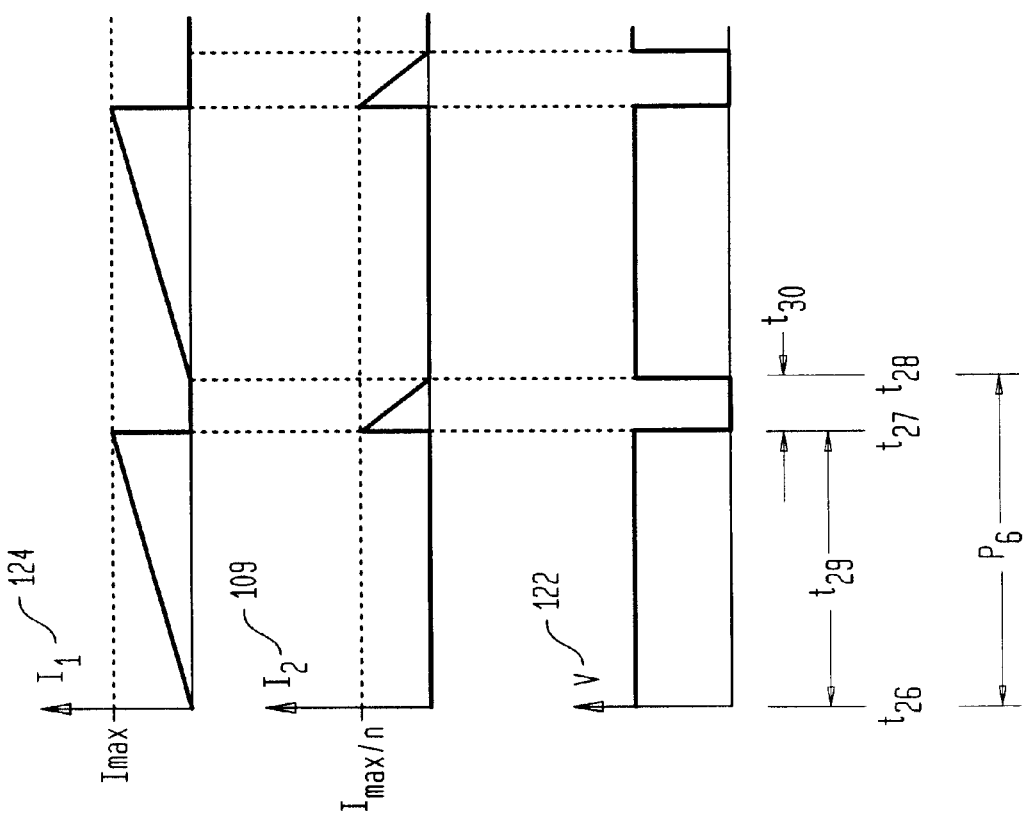

FIGS. 2F and 2G show two time periods in which transformer 114 is controlled in accordance with the discontinuous mode. During each charge cycle substantially all energy in transformer core 105 is transferred to capacitor 108. Although the "off time" of the primary charge cycle was limited to a maximum time duration, there is no lower limit to the off time. The portion of the charge cycle during which energy is transferred to capacitor 108 continues to decrease, then, since the energy stored in capacitor 108 continues to increase. This is because capacitor 108 can store a greater quantity of energy than that stored in transformer core 105.

Thus, time durations $t_{30}$ and $t_{35}$ are increasingly shorter in duration than the previous occurring time periods $t_{25}$, $t_{20}$, etc. There is no corresponding increase in the time periods during which the transformer is charged. This is because primary current 124 repeatedly increases from zero to $I_{max}$ since the condition illustrated in FIG. 2E. As a result, the period of each charge cycle, $P_5$ and $P_6$, are shorter than the preceding charge cycle periods, $P_1$–$P_5$. In other words, the frequency of the charge cycles increases during the discontinuous mode of operation. This progression continues until capacitor 108 is completely charged.

Figure 3:
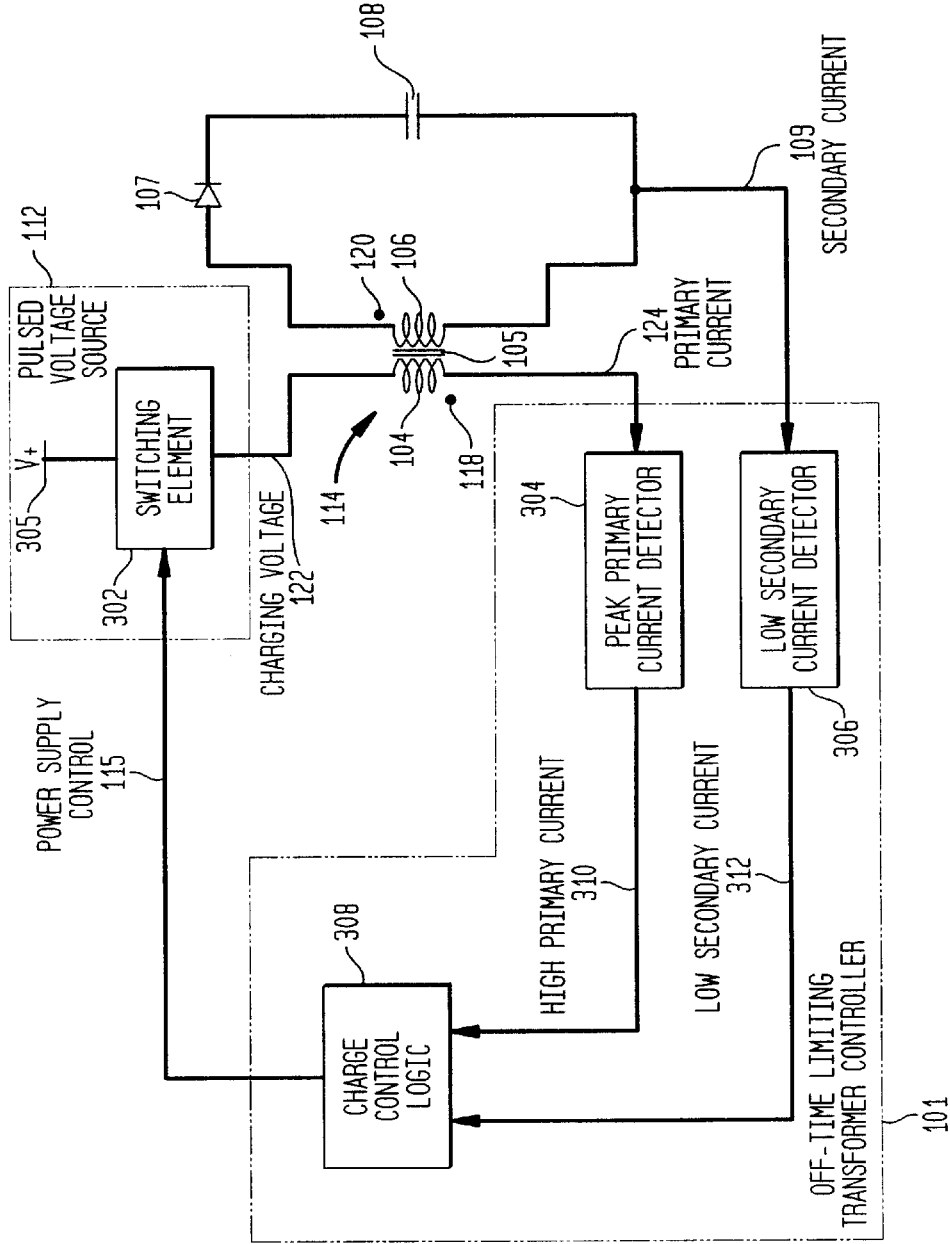
FIG. 3 is a block diagram of one embodiment of the transformer controller illustrated in FIG. 1B.
Figure 4:
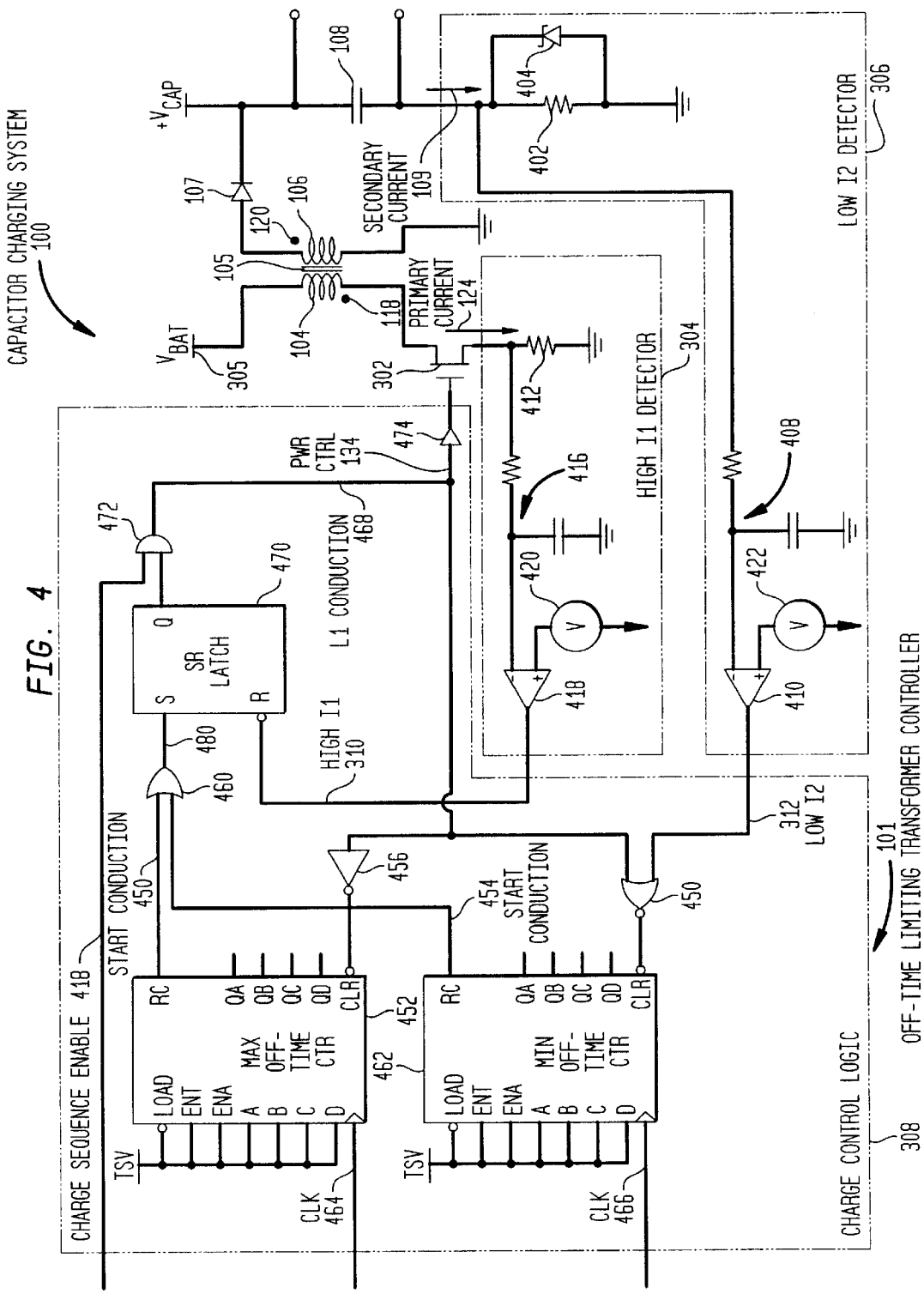
FIG. 4 is a schematic block diagram of one implementation of a capacitor charging system of the present invention.

One exemplary implementation of capacitor charging system 100 will now be described with reference to FIGS. 3 and 4. FIG. 3 is a block diagram of one embodiment of capacitor charging system 100 of the present invention. FIG. 4 is a more detailed schematic block diagram of one implementation of the capacitor charging system illustrated in FIG. 3.

Referring to FIG. 3, in this illustrative embodiment, pulsed voltage supply 102 includes a constant voltage source 305 and a switching element 302 connected in series between voltage source 305 and primary winding 104. Switching element 302 is controlled by transformer controller 101 to apply power to transformer 114. Switching element 302 interrupts the electrical connection between voltage source 305 and primary winding 104 in response to a control signal 115 to effect a desired change in the frequency and duty cycle of voltage signal 122 and, hence, primary current 124. Switching element 302 preferably includes a switch that provides a small series resistance to the anticipated primary current 124 such that there is a minimal voltage drop across switching element 302. This allows substantially all the voltage generated by voltage source 305 to be applied to primary winding 104.

In addition, switching element 302 is preferably characterized by a turn-off time sufficiently fast to substantially avoid over-charging and saturating transformer core 105. As would be obvious to one of ordinary skill in the art, many other implementations of switching element 302 now or later developed may be utilized in accordance with the present invention. Switching element 302 may be any high voltage switch. In the implementation illustrated in FIG. 4, for example, switching element 302 is shown as a MOSFET.

A MOSFET switching transistor 302 has a sufficient current capacity to switch the selected maximum primary current 124 through primary winding 104 and is likely to withstand transient currents caused by the inductance when the voltage applied to primary winding 104 transitions. In one embodiment of the present invention, MOSFET switching transistor 302 is an IRF2807 transistor manufactured by International Rectifier, Inc. MOSFET switching transistor 302 preferably has a transient suppressor diode (not shown) connected across the drain and source nodes of the transistor in order to provide a current path for discharging primary winding 104 when voltage source 305 is disconnected from the primary winding 104. This is to prevent a leakage inductance of the primary winding 104 from generating a voltage sufficiently high to destroy MOSFET switching transistor 302. Constant voltage source 305 may be any source of substantially constant power such as a battery, a direct current power supply, etc. In one embodiment, voltage source 305 is a lithium battery.

In this illustrative embodiment, transformer controller 101 includes a power supply control logic circuit 308 that controls pulsed voltage source 102. A peak primary current detector 304 detects when primary current 124 exceed a predetermined maximum threshold indicating that the conduction time of primary winding 104 is completed. Peak primary current detector 304 generates a high primary current signal 310 that is utilized by charge control logic 308 as described in detail below. In addition, transformer controller 101 includes a low secondary current detector 306 that detects when secondary current 109 falls below a predetermined minimum threshold value indicating that the off-time of a charge sequence is completed. Low secondary current detector 306 generates a low secondary current signal 312 that is utilized by charge control logic 308 to generate power supply control signal 115.

During a charge cycle, control logic 308 turns on MOSFET 302, causing primary current 122 to flow through primary winding 104. During this on-time portion of the charge cycle, current 124 is increasing. When detector 304 indicates that primary current 122 has reached a maximum value, control logic 308 turns off MOSFET 302, causing primary current 122 to cease. During this off time of the primary current charge cycle, secondary current 109 stepwise transitions to a current value and decreases linearly as energy is transferred to capacitor 108. Control logic 308 ceases the off-time and begins another charge cycle either when the predetermined maximum off time transpires or transformer core 105 transfers substantially all of its energy to capacitor 108, identified by secondary current 109 decreasing to some value close to zero. The former condition occurs during continuous mode while the latter occurs during the discontinuous mode of operation.

FIG. 4 is a schematic block diagram of one embodiment of a capacitor charging system 100 of the present invention. Capacitor charging system 100 includes specific implementations of charge control logic circuit 308, high primary current detector 304 and low secondary current detector 306. Referring to FIG. 4, this embodiment of charge control logic circuit 308 is implemented with two counters. Counter 452 maintains the off time of the charge cycles to within a maximum time duration, curtailing the initially applied charge cycles that have extended off-times due to the initial low capacitor voltage. Counter 462 is an optional counter that sets a minimum time duration of the same off-time portion of the charge cycle. Each of these counters 452 and 462 have programmable clock inputs 464, 466, respectively, through which an operator can program or otherwise control the operation of capacitor charging system 100. In addition to the two programmable clock inputs 464 and 466, a charge sequence enable signal 418 is provided to enable the operator to initiate and maintain a charge sequence. In the following description, counters 452, 462 and detectors 304, 306 are first described in detail. Then the configuration of circuit 100 and its operation will be presented.

Counters 452, 462 are well-known and commonly available 4-bit binary counters that can be cleared asynchronously. Counters 452, 462 have a load, enable and four data input ports by which counters 452, 462 are controlled. Each counter 452, 462 also has a clock input port and a clear input port. Counters 452, 462 continuously count, with the associated generation of start conduction signals 458, 454, until a clear signal is received at the clear (CLR) port or the associated clock signal is no longer applied. Upon receipt of a clear signal, which is active low, the 4 bits within the counter are cleared and the counter is reset to zero. As long as the clear signal is active the counter will remain in the cleared or reset state. When the clear signal is not active, the counters 452, 462 increment at the frequency of the respective clock input 464, 466. Counters 452 and 462 also have 4 data output ports and a ripple carry (RC) output port. Counters 452, 462 generate periodically a ripple carry (RC) signal. The period of the ripple carry signal is 16 periods (4 bits) of the respective input clock signal 464, 466. The two input clock signals are programmable using any well-known technique.

In this embodiment, the data, load and enable inputs of each counter 452, 462 25 are connected permanently to a high voltage source as shown in FIG. 4. In addition, the four data output ports are not used in this embodiment of the invention. As a result, counters 452, 462 simply count from 0 to 15 when the counters are not in the clear state. That is, when the active low clear signal is no longer received, the counters begin counting from 0 to 15. Upon reaching 15, each counter asserts the ripple carry signal. As shown in FIG. 4, the ripple carry signal generated by counter 452 is referred to as a start conduction signal 458. Counter 452 controls the maximum off-time duration by starting a new charge cycle by generating start conduction 458 once the off-time has reached the maximum off-time duration. Similarly, the ripple carry signal generated by counter 462 is referred to as start conduction signal 454. Here, counter 462 imposes a minimal time delay between successive charge cycles to avoid damaging zener diode 404 by generating start conduction 454 some predetermined time after the ceasing of the off-time portion of the previous charge cycle.

As noted, the frequency of start conduction signals 458 and 454 are programmable through the selection of the frequency of clock signals 464 and 466, respectively. As one example, counter 452, which controls the off time of primary winding current 122, is on the order of microseconds. The frequency is tailored to the implemented transformer, battery voltage and other characteristics of the implementing circuit, as one of ordinary skill in the art would appreciate. For example, for counter 452 to generate a start conduction signal approximately 10 microseconds after the removal of the clear input, clock 416 would be a 1.6 MHz clock signal.

Counter 462, on the other hand, is utilized to insure the operation of charge control logic 308 is not adversely affected by the recovery time of diode 404, a phenomenon described in detail below with reference to detector 306.

Accordingly, counter 462 applies start conduction signal 454 on the order of tens of nanoseconds after the clear input is de-asserted. For example, to provide a start conduction signal 454 having an 200 nanosecond period, clock 466 would be an 80 MHz clock signal. The frequency of clock signal 466 may be tailored to the type of diode 107 selected and other characteristics of the implementing circuit, as one of ordinary skill in the art would appreciate. The operation of counters 452 and 462 will be provided in detail below.

In the illustrative embodiment, counters 452 and 462 are National semiconductor 74HC161 Synchronous Binary Counter with Asynchronous Clear counters. However, it should be understood that many manufacturers make such a device and that the functionality of such a device may be implemented in, for example, an ASIC.

Referring now to the current detectors, there are two current detectors 304, 306 implemented in this embodiment of charging system 100. In this particular embodiment, detectors 304 and 306 have been implemented with similar components in a similar configuration. Referring to high primary current detector 304, detector 304 includes a primary current sensor 412 implemented as a sense resistor connecting primary current 124 to ground. A low pass filter 416 couples the voltage produced across sense resistor 412 to a negative input of a voltage comparator 418. The positive input of comparator 418 is connected to a reference voltage 420. When the magnitude of primary current 124 is greater than reference voltage 420, comparator 418 generates high primary current signal 310. Reference voltage 420 is selected such that this occurs when primary current 124 reaches $I_{max}$, The manner in which high primary current signal 310 is used by control logic 308, is described in detail below.

When primary winding 104 is switched on, a current spike may result at the instant the voltage increases. This current spike may be cause by, for example, the reverse recovery of diode 107. Filter 416 is designed to filter out this spike without substantially affecting the remainder of the signal. In one embodiment of the present invention, filter 416 is a single pole R-C low-pass filter. It would be obvious to those of skill in the art that other filters may be used as well. For example, active analog low-pass filters, switched capacitor filters, or digital filters could be used. In one embodiment, a digital blanking filter is used. The digital blanking filter would sample the waveform at sense resistor 412, and would provide a low output to comparator 418 until the digital filter determined that the current spike had passed. The digital filter would then pass the voltage signal without any attenuation or phase distortion. In another embodiment, the digital blanking filter would ignore the magnitude of the waveform for a predetermined period of time. After the predetermined time has passed, the blanking filter would then pass the voltage signal without attenuation.

Voltage comparator 418 in one embodiment of present invention may be selected on the basis of the speed at which it changes state and the amount of overshoot that occurs during the switching process. It is important for comparator 418 to have a faster response time than the rate at which primary current 124 increases to avoid potential damage to charge control logic 308. In one preferred embodiment of present invention voltage comparator 418 is a Max998 comparator manufactured by Maxim, Inc.

Similarly, low secondary current detector 306 receives secondary current 109 and generates a low secondary current signal 312 when secondary current 109 falls below a predetermined threshold value of approximately zero, indicating that substantially all of the energy stored in transformer core 105 has been transferred to capacitor 108. Detector 306 includes a sense resistor 402 connecting secondary current 109 to ground. A zener diode 404 is connected in parallel with sense resistor 402.

A filter 408 operates in a manner similar to filter 416, presenting a secondary current magnitude signal to a positive input of a comparator 410. The negative input of comparator 410 is connected to a reference voltage 422. When the magnitude of secondary current 109 falls below reference voltage 422, comparator 410 generates a low secondary current signal 312. The manner in which low secondary current signal 312 is utilized by charge control logic 308 is described in detail below.

Zener diode 404 clamps the voltage across sense resistor 402 that is applied to comparator 410 to prevent the input voltage limit of comparator 410 from being exceeded. In one embodiment, the threshold is 100 mv; that is, when secondary current 109 drops down so that the voltage across sense resistor 402 is approximately 100 mv, then low secondary current signal 312 is generated indicating that secondary winding 106 has stopped conducting.

In this embodiment, capacitor charging system 100 includes a voltage source 305 connected to one node of primary winding 104. A MOSFET 302 is connected between the other node of primary winding 104 and ground. The state of MOSFET 302 controls the conduction of primary winding 104. MOSFET 302 is controlled by other components of charge control logic 308 based in part on the magnitude of primary current 124 and secondary current 109 and the duration of the off-time of the primary winding current waveform charge cycle.

As noted, transformer 114 is controlled by charge control logic 308. Generally, during a charge cycle, control logic 308 turns on MOSFET 302, causing primary current 124 to flow through primary winding 104. When detector 304 indicates that primary current 124 has reached a maximum value, control logic 308 turns off MOSFET 302, causing primary current 124 to cease and the charge cycle on time to end. During the subsequent charge cycle off time, secondary current 109 first stepwise transitions to a current value as described above with reference to FIGS. 2A–2G, and decreases linearly as energy is transferred to capacitor 108. Control logic 308 ceases the charge cycle off time and begins another charge cycle either when the predetermined maximum off time transpires or transformer 105 transfers substantially all of its energy to capacitor 108, identified by secondary current 109 decreasing to some value close to zero. The former occurs during the continuous mode while the latter occurs during the discontinuous mode of operation.

Off time limiting counter 452 generates a start conduction signal 458 at its ripple carry (RC) output port when primary current 124 is to be conducted through primary winding 104. Start conduction signal 458 is provided to one input of an OR gate 460. The other input of OR gate 460 is connected to the ripple carry (RC) output port of minimum off-time counter 462. Thus, start conduction signal 458 and start conduction 454 are provided to OR gate 460 having an output connected to the set (S) input port of a reset dominant set-reset (S-R) flip-flop 470.

The output of high primary current detector 304 is connected to a reset (R) input of S-R flip-flop 470. As shown in FIG. 4, the reset input requires an active low signal. The output of S-R flip-flop 470 is received at one input of an AND gate 472. The other input of AND gate 472 is provided with externally-controlled charge sequence enable signal 418. The output of AND gate 472, referred to herein as L1 conduction signal 468, controls a gate driver 474 suitable for driving MOSFET 302. L1 conduction signal 468 is also provided to the clear (CLR) input of off-time limiting counter 452, which also requires an active low signal to be enabled. L1 conduction signal 468 is inverted by inverter 456 prior to being provided to the active low clear input of counter 452. Thus, when L1 conduction signal 468 is asserted (that is, when primary winding 104 is conducting), counter 452 is held in a clear state. Conversely, when the conduction signal is de-asserted (that is, primary winding 104 is not conducting—the off-time of the charge cycle), counter 452 is counting.

The output of AND gate 472 is NOR'ed with low secondary current signal 312 generated by secondary current detector 306. Low secondary current signal 312 is asserted when substantially all the energy stored in transformer core 105 has been transferred to capacitor 108. Thus, counter 462 counts when L1 conduction signal 468 is de-asserted (that is, primary winding 104 is not conducting) and when secondary current 109 is not zero (that is, when energy is being transferred from transformer core 105 to capacitor 108). Counter 462 is cleared when L1 conduction signal 468 is asserted (that is, primary winding 104 is conducting) or when secondary current 109 is flowing.

In operation, charge sequence enable signal 418 is initially de-asserted. L1 conduction signal 468 is likewise de-asserted causing power control signal 134 to turn off MOSFET 302. Primary current 124 is, therefore not flowing through primary winding 104. With no energy stored in transformer core 105, secondary current 109 is also zero and the output of detector 306, low secondary current 312, is asserted. Counter 462, therefore, counts from 0 to 15, generating periodically a start conduction signal 454. On the other hand, the de-asserted L1 condition signal 468 is inverted by inverter 456 and applied to the clear input of counter 452. This maintains counter 452 in a clear state until L1 conduction signal 468 is asserted. After one period of counter 462, start conduction signal 454 is asserted. This causes signal 480 generated by AND gate 460 to set S-R flip-flop 470. The output of S-R flip-flop 470 is thereafter maintained in the asserted state until reset by detector 304 indicating the completion of the charge cycle on time.

At some later time charge sequence enable signal 418 is asserted. This causes AND gate 472 to assert L1 conduction signal 468. Gate driver 474 turns on MOSFET 302 causing primary current 124 to flow through primary winding 104. The asserted L1 conduction signal 468 is also presented to NOR gate 450 which does not alter the state of the clear input to counter 462 due to the asserted state of low secondary current signal 312. The asserted L1 conduction signal 468 is inverted by inverter 456, serving to reset counter 452. Primary current 124 begins to flow at a substantially consistent rate as described above. Thus, during the on-time of each charge cycle, both counters 452 and 462 are held in the clear state.

When primary current 124 reaches $I_{max}$, detector 304 de-asserts high primary current signal 310. Signal 310 resets S-R latch 470 causing L1 conduction signal 468 to be de-asserted. This turns off MOSFET 302, ending the on-time portion of the charge cycle. The de-asserted L1 conduction signal 468 is inverted by inverter 456, taking counter 452 out of the clear state. Counter 452, therefore, begins to count as described above. Similarly, de-asserted primary winding conduction signal 468 is applied to NOR gate 450. Since low secondary current signal 312 is also de-asserted, the output of NOR gate 450 is asserted, taking counter 462 momen-tarily out of the clear state. Counter 462 also begins to count as described above. When secondary current 109 begins to flow, counter 462 is again placed on the clear state.

As noted, during the off-time of primary current 124 waveform, secondary current 109 flows through secondary winding 106. During the initial portion of the charge sequence, current 109 flowing in secondary winding 106 decreases slowly due to the minimal energy currently stored in capacitor 108. As a result, counter 452 generates a start conduction signal 458 before detector 306 indicates secondary current 109 has decreased to approximately zero. When start conduction signal 458 is asserted, the output of OR gate 460 is asserted, setting S-R latch 470. Since enable signal 418 is still asserted, this causes the start of a new charge cycle and the clearing of the two counters 452 and 462. In other words, the charge cycle off-time is limited to a maximum time duration of the period of start conduction signal 458.

This process continues until the discontinuous mode portion of the charge sequence is invoked by charging system 100. The discontinuous mode begins when transformer 114 can transfer its stored energy from core 105 to capacitor 108 within the maximum off-time period. When this occurs, detector 306 asserts low secondary current signal 312. This causes counter 462 to begin counting, asserting start conduction signal 454 in, for example, 200 nanoseconds. Thus, start conduction signal 454 is asserted 200 nanoseconds after secondary current 109 reaches zero. This 200 nanosecond delay allows for diode reverse recovery time of diode 107. This process continues until capacitor 108 is fully charged.

Diode 107 is a high voltage diode constructed of a stack of one or more silicone junctions. For example, diode 107 may include 5 stacked junctions each with a breakdown voltage of 1200 volts, for a total breakdown voltage of 6000 volts. There may be a mismatch in timing of these junctions causing one junction to turn off before the others. When the diode is reversed, that faster junction will have applied to it the entire capacitor voltage for the brief period until the other junctions turn off. Counter 462 provides a delay of, for example, 200 nanosecond, to insure no one single unction will be exposed to such high voltages. In other words, by providing a delay, the reverse recovery time of all junctions of diode 504 can transpire, allowing all the junctions to shut off before the diode is exposed to the capacitor voltage.

Figure 5:
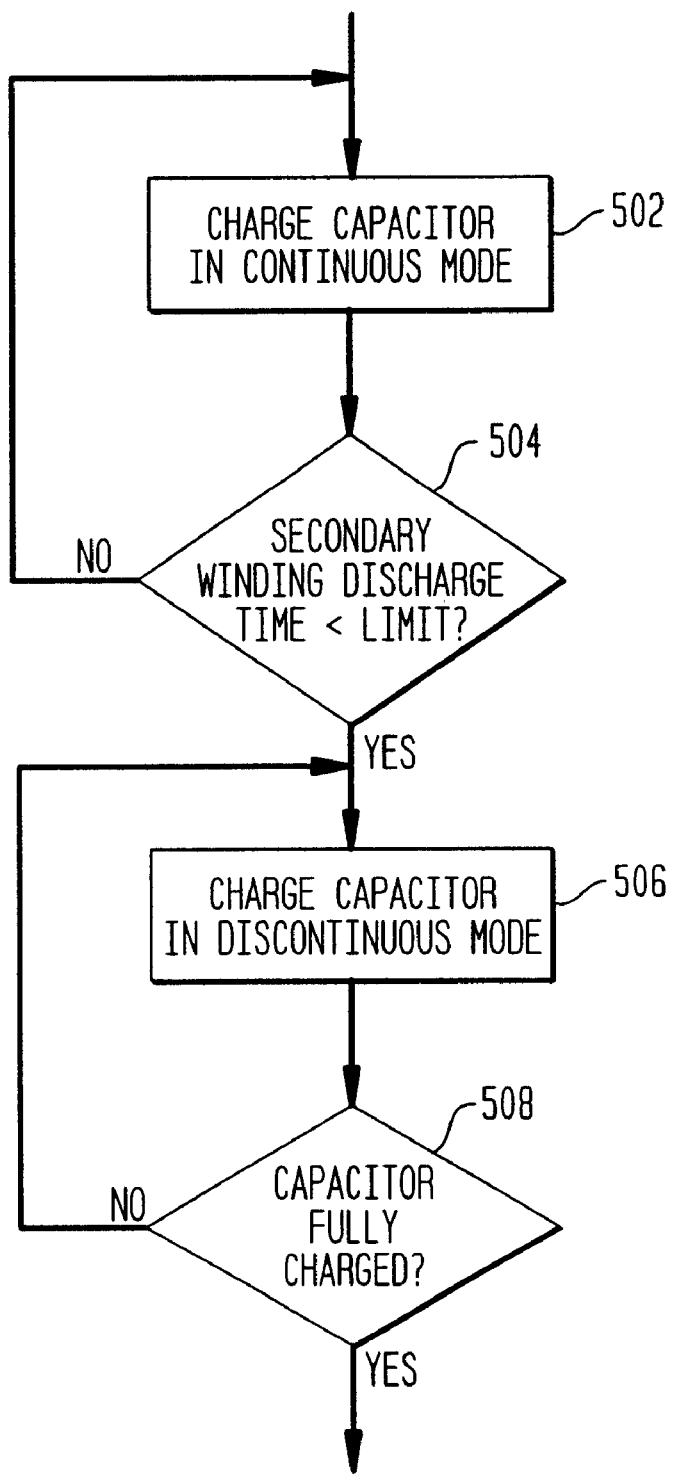
FIG. 5 is a flowchart of a methodology to charge a capacitor in accordance with one embodiment of the present invention.

FIG. 5 is a flow chart illustrating the processes performed to charge a high voltage capacitor for in accordance with one embodiment of the present invention. At step 502 capacitor 108 is charged in accordance with the continuous mode of operation. Here, as noted, charge cycle off time is limited to a predetermined maximum time duration. This prematurely ends the off time of those charge cycles that occur early in a charge sequence when the capacitor has minimal stored energy. Such charge cycle off times are substantially lengthy and significantly longer than the predetermined maximum time.

At step 504 the time to discharge secondary winding 106 is monitored. This, as noted, is the off time of the primary current charge cycle. If the time is less than the maximum time limit, then capacitor 108 continues to be charged in accordance with the continuous mode of operation. When it is determined at step 504 that the discharge time of the secondary winding is less that the maximum time limit, then processing continues at step 506. At step 506 the capacitor is charged in discontinuous mode. This continues until capacitor 108 is fully charged, as determined at step 506.

Step 506 is repeated until step 508 determines the capacitor is fully charged. As noted, in those applications in which capacitor 108 becomes fully charged during the continuous mode of operation, there will be no discontinuous mode of operation and steps 506 and 508 are not performed.

As one of ordinary skill in the art would find apparent, there are many other implementations of charge control circuit 308. For example, in embodiments in which the noted issues regarding diode 107 are not of concern, counter 462 and NOR gate 450 may be eliminated, and low secondary current signal 312 may be provided to OR gate 460 as start conduction signal 458.

It should also be apparent that the embodiment illustrated in FIG. 4 is just one example of how one may implement charge control logic 308, and that it depicts only the functionally relevant portions thereof. For example, certain embodiments include additional components to compensate for the propagation delay between L1 conduction signal 468 and low secondary current signal 312, as applied to NOR gate 450. There is a limitation of the period of counter 462 derived from the time it takes for MOSFET 302 to be turned off, transformer 114 to fly back, the current to flow through sense resistor 402 and the assertion of signal 312 by comparator 410. This propagation delay between the two inputs of NOR gate 506 has to be less than the programmed period of clock 524. In one embodiment, charge control logic 308 is implemented in an ASIC. In such an embodiment, a delay element or component may be added to the line carrying L1 conduction signal 420 to NOR gate 450. It should also be understood that capacitor charging system 100 may alternate randomly between the continuous and discontinuous modes during the transition period from the former to the latter.

Transformer 114 is selected according to several design trade-offs. One desirable characteristic of transformer 114 is that it have a high turns ratio. Such a transformer produces a high output voltage for a much lower applied or input voltage. In addition, in the disclosed aspects of the capacitor charging system 100, the windings of transformer 114 are of opposite polarity. This results in little or no current flowing in secondary winding 106 of the transformer while primary winding 104 is accumulating energy. When primary winding 104 has completed its charge cycle and is turned off, secondary winding 106 will then transfer energy into capacitor 108, as described above. In selecting the size of transformer 114 several factors should be considered. For example, the energy storage within core 105 of transformer 114 is a function both of the inductance of primary winding 104 and the voltage that is applied to it. In general, the larger the core 105 of transformer 114, the more energy that may be stored within the magnetic field surrounding it. In addition, there is a current at which magnetic core 105 of transformer 114 will saturate; applying a current above this value will not improve circuit performance. In general the larger the transformer core, the higher the saturation current. Therefore, selection of transformer 114 will often times involve balancing physical and electrical requirements of the system. A larger transformer will allow lower frequencies to be used because the larger transformer will be able to utilize larger currents and will therefore transfer energy at a greater rate per cycle than a smaller transformer. This reduces the demand on the supporting components; they may operate, for example, at a lower speed. However, a larger transformer will occupy a large volume of space, weigh more, and may produce more heat and may produce electrically interfering noise if large currents are passed through it. On the other hand, a smaller transformer will require higher frequencies in order to transfer an equivalent amount of energy. This is because a smaller transformer utilizes lower currents and hence transfers energy at a lower rate per cycle. However, using a lower off-time period to achieve an equivalent rate of energy transfer requires greater complexity due to parasitic characteristics, noise sensitivity, etc. In one embodiment of the present invention, transformer 114 has an Lp of approximately 8 $\mu$H and a turns ratio of 1:38 (primary:secondary).

It should be understood that, as noted, capacitor charging system 100 may take on any other configurations and implementations. For example, other circuit configurations and components may be used in addition to or instead of the above-noted configurations and components. For example, other magnetic elements such as a single inductor may be used.

The present invention is related to U.S. Utility Patent Application entitled "System and Method for Charging A Capacitor Using a Constant Frequency Current Waveform," filed concurrently herewith under Attorney Docket No. 10980557-1, and naming as inventor Gregory D. Brink, the specification of which is incorporated by reference herein in its entirety.

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A capacitor charging system, connected electrically to a capacitor, constructed and arranged to charge the capacitor by generating a variable frequency, variable duty cycle current waveform.

2. The system of claim 1, wherein the system generating a charge sequence of successive current charge cycles, and wherein the system comprises:
   a transformer having a primary winding connected in series to a voltage source and a secondary winding across which the capacitor is electrically coupled; and
   a controller for controlling a primary current through said primary winding such that during each of a first plurality of charge cycles of the charge sequence said transformer does not transfer all stored energy to the capacitor, and during each of a subsequent plurality of charge cycles of the charge sequence said transformer transfers substantially all stored energy to the capacitor.

3. The system of claim 2, wherein said transformer is a fly-back transformer, wherein said controller comprises:
   a first current detector configured to determine when said primary current achieves a maximum current; and
   a second current detector configured to determine when current flowing through said secondary winding is approximately zero
   wherein said controller controls said primary current based at least in part on whether said primary current has achieved said maximum value and whether said secondary current is approximately zero.

4. A high-voltage capacitor charging system constructed and arranged to generate current pulses having a variable frequency to charge a capacitor, wherein during a charging sequence in which said current pulses are repeatedly applied to the capacitor, the duty cycle of the variable frequency current waveform is controlled dynamically based on the rate at which energy can be transferred to the high voltage capacitor.

5. A system for charging a high-voltage capacitor comprising:
- a fly-back transformer having a primary winding, a core and a secondary winding that is out of phase with said primary winding, with the capacitor electrically coupled across said secondary winding; and
- a charge controller for applying a charge sequence of successive current charge cycles to said primary winding, each charge cycle having an on time and an off time, wherein for each said charge cycle on time said controller enables said primary current to flow through said primary winding until said primary current reaches a maximum current, and for each said charge cycle off time said controller inhibits said primary current until either current through said secondary winding is approximately zero or a predetermined maximum charge cycle off time has transpired.

6. The system of claim 5,
- wherein, for a first plurality of charge cycles said maximum off time transpires prior to said secondary winding current becoming approximately zero, resulting in said transformer storing energy in said core during each of said first plurality of charge cycles, and
- wherein, for a second plurality of charge cycles occurring subsequent to said first plurality of charge cycles, said secondary winding current becomes zero prior to said maximum off time transpiring, resulting in said transformer transferring substantially all stored energy during of said second plurality of charge cycles.

7. The system of claim 6, wherein said charge controller comprises:
- a power supply for generating a voltage across said primary winding;
- a first current detector configured to determine when said primary current achieves a maximum current;
- a secondary current detector configured to determine when current flowing through said secondary winding falls below a minimum current; and
- control logic that controls said primary current based on whether said primary current has achieved said maximum value and a relative timing between when said secondary current reaches approximately zero and said maximum time duration.

8. The system of claim 7, wherein said power supply comprises:
- a power source for providing a voltage and a current;
- a switching element connected in series with the power source and said primary winding, wherein said switching element controls said current flowing in said primary winding.

9. The system of claim 8, wherein said switching element comprises:
- a switching transistor.

10. The system of claim 9, wherein said switching transistor is a MOSFET.

11. The system of claim 8, wherein said control logic comprises a counter having a programmable clock input wherein said counter generates a signal having a period set to said maximum time duration.

12. A method for charging a capacitor comprising the steps of:
- providing a fly-back transformer having a primary winding, a core and a secondary winding that is out of phase with the primary winding;
- applying a charge sequence of successive current charge cycles to the primary winding, such that for each charge cycle on time the primary current is applied until the primary current reaches a maximum current, and for each charge cycle off time the primary current is inhibited until either current through the secondary winding is approximately zero or a predetermined maximum charge cycle off time has transpired.

13. The method of claim 12, wherein said maximum charge cycle off time is of a duration such that for a first plurality of charge cycles the maximum off time transpires prior to the secondary winding current becoming approximately zero, resulting in the transformer storing energy during each of the first plurality of charge cycles, and for a second plurality of charge cycles occurring subsequent to the first plurality of charge cycles, the secondary winding current becomes zero prior to the maximum off time transpiring, resulting in the transformer transferring substantially all stored energy during the second plurality of charge cycles.

* * * * *